United States Patent [19]

Curchack

[11] 4,413,741
[45] Nov. 8, 1983

[54] HANGER ASSEMBLY FOR BOTTLES

[75] Inventor: Leon T. Curchack, Los Angeles, Calif.

[73] Assignee: Baxter Travenol Laboratories, Inc., Deerfield, Ill.

[21] Appl. No.: 331,332

[22] Filed: Dec. 16, 1981

[51] Int. Cl.³ ............................................. B65D 25/22
[52] U.S. Cl. ................................. 215/100 R; 248/359
[58] Field of Search ..................... 215/100 R, 100 A; 16/222, 225; 248/359, 360

[56] References Cited

U.S. PATENT DOCUMENTS

| | | | |
|---|---|---|---|
| 2,635,604 | 4/1953 | Fredrickson | 215/100 A X |
| 2,652,054 | 9/1953 | Bishop | 215/100 A |
| 3,384,258 | 5/1968 | Singer | 215/100 A |
| 3,387,732 | 6/1968 | Jellies | 215/100 A |
| 3,635,367 | 1/1972 | Morita et al. | 215/100 A |
| 3,807,679 | 4/1974 | Burke et al. | 215/100 A X |
| 3,901,399 | 8/1975 | McPhee | 215/100 A |
| 4,010,862 | 3/1977 | Gilbert | 215/100 A |
| 4,090,729 | 5/1978 | Erickson | 215/100 A X |

FOREIGN PATENT DOCUMENTS 2806391  8/1978  Fed. Rep. of Germany ... 215/100 R

OTHER PUBLICATIONS

"Tenite Plastic Technical Report", TR-14B Kodak, May, 1972.

Primary Examiner—William Price
Assistant Examiner—Sue A. Weaver
Attorney, Agent, or Firm—Paul C. Flattery; Lawrence W. Flynn; Max D. Hensley

[57] ABSTRACT

An improved hanger assembly is provided for use with bottles containing liquids, particularly glass vessels for holding liquids to be administered parenterally. The hanger includes a frangibly-activated hinge that biases the rotation of a hook or loop into a position to enable safe and expeditious hanging of the bottle. The assembly is a substantially rigid unitary construction made of material having a substantially uniform thickness, i.e., not having any elements protruding outside of the general profile of the bottle to be hung. The assembly maintains this profile until the frangibly-activated hinge is broken to allow rotation of the hook or loop into a position to permit hanging. Further, use of a frangibly-activated hinge permits the use of design and materials for the hanger assembly which reduce the risks of tearing the hanger and improve the bottle orientation when it is hung.

25 Claims, 4 Drawing Figures

HANGER ASSEMBLY FOR BOTTLES

DESCRIPTION

This invention relates to hangers for containers, especially those liquid containers which require hanging by their bases. In particular, the field of this invention consists of hanging assemblies which attach to glass bottles of parenteral solutions for suspending the bottles during administration of the solutions.

Parenteral solution containers are generally glass or plastic bottles having a hanger molded into or attached to the base. The contents of a parenteral solution bottle are conventionally administered to a patient by resting the bottle on its base while puncturing or otherwise accessing the contents with a liquid flow conduit called an administration set, suspending the bottle by its base hanger at a point above the patient, accessing the patient's veins with the administration set and then allowing the contents to flow into the patient's vein.

Such bottles have been suspended by a wide variety of hangers, most of which involve a band which envelopes the bottle to a greater or lesser degree and a bail or handle that is connected to the band in various ways. For example, see U.S. Pat. Nos. 3,807,679; 3,635,367; and 2,652,054. Since thermoplastic bottles have become widely accepted many hanging systems are molded integrally with the bottle. Examples of such integral structures are illustrated in U.S. Pat. Nos. 3,384,258; 4,010,862; 3,387,732; and 3,901,339.

The known hanging structures are deficient from the point of view of ease and cost of manufacturing, safety and reliability, and user convenience. These deficiencies are particularly important in the medical industry where many of the products contained within the bottles are biologically active substances such as drugs to which attending staff or other patients should not be exposed by way of breakage due to accidental failure of a hanger assembly. Further, the hangers must be convenient to use, otherwise medical therapy will be proportionately delayed. Finally, the hangers should be constructed so that the containers are suspended entirely vertically, whatever the weight of fluid remaining in the bottle. This will ensure that the bottle graduation markings remain horizontal and parallel with the fluid meniscus throughout fluid administration. This eliminates guess-work in reading the level of fluid as it is administered and guarantees fluid drains from the bottle completely.

Accordingly, it is an object of this invention to provide a hanging assembly which is less costly to manufacture than heretofore existing systems.

It is another object of this invention to hang containers with less risk of rupture in the hanging systems than is attendant present systems.

A further object of this invention is to hang liquid containers vertically whatever the fluid level within the containers.

Another object is to eliminate protrusions from the general profile or outline of the containers so as to prevent inadvertent hooking or catching of the protrusions on obstacles and the resulting breakage or rupture of the container or its hanging assembly.

These and other objects of the invention will be apparent from consideration of this specification as a whole.

SUMMARY OF THE INVENTION

This invention provides an improved hanger assembly in which a tab containing a frangibly-activated hinge and a suspension means is molded or bonded to a skirt. The skirt is connected to a container or molded integrally with a container. The improved hanger assembly is compact and of substantially uniform thickness except where it is compact and pierced by passages or openings, i.e., no protrusions exist beyond the profile of the container to which the system is adapted. Thus the container may be rested on the hanger assembly without tipping over. It also needs no fasteners to hold elements of the hanger in place. The hinge has been found to be extremely reliable through multiple flexings and is effective in biasing the suspension means of the hanger into a vertical position convenient for rapid hanging and set up. An additional advantage is that the container can be rested on the hanger even after the hinge has been frangibly activated and the suspension means extended.

THE DRAWINGS

DESCRIPTION OF THE PREFERRED EMBODIMENTS

Figure 1:
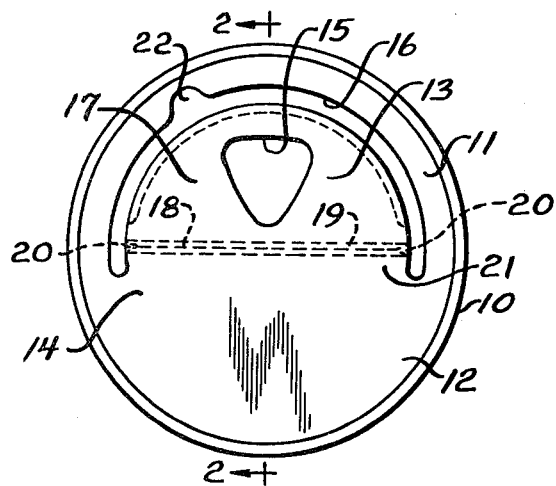
FIG. 1 is a top elevational view of the hanger assembly.

FIG. 1 shows the hanger assembly as viewed from the bottom of a bottle or container (not shown) onto which it is engaged or into which it is integrally molded. A cylindrical skirt 10 depends from a flange 11 which projects inwardly of the upper skirt rim 12.

The flange 11 is enlarged over about 40% of its circumference to accommodate a tab 13 at a connecting region 14. The tab 13 includes a suspension means generally shown at 17, in this figure including a thickened loop 16 and a generally triangular hole 15 embraced by the loop which has dimensions that conform with conventional parenteral solution bottle hanging bars, rods or hooks.

The tab 13 also includes a frangibly-activated hinge 18. The hinge 18 comprises a generally V-shaped score 19 located across the center axis of the skirt 10 and penetrating at maximum depth about one-half of the way through the tab from the side of the tap opposite the upper skirt rim 12. The hinge 18 includes a bridge 20 or thickened region of the tab at the score line, one bridge being located at each end of the score 19 to aid in ensuring that the hinge will remain rigid until frangibly activated. A resilient lip 21 is interposed between the hinge 18 and the connecting region 14 to relieve stress on the hinge during activation and hanging. The arcuate opening defined by the arcuate flange 11 is only as wide as is necessary to allow rotation of the suspension means, about the hinge, although it may have an expanded area 22 where part of the flange 11 has been removed so as to allow entry of a prying means such as a finger (not shown) to frangibly activate the hinge.

Figure 2:
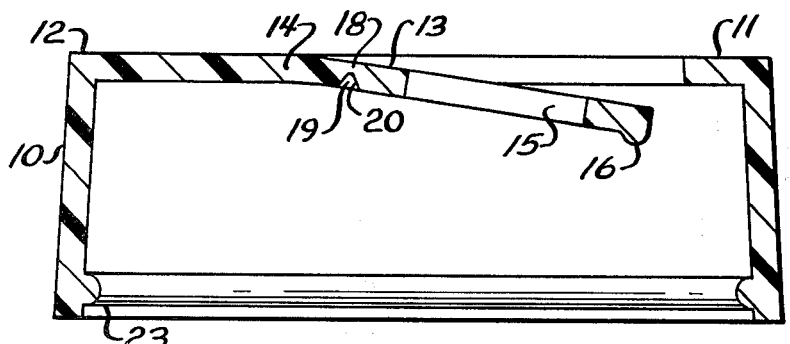
FIG. 2 is an enlarged sectional view taken along line 2—2 of FIG. 1.
Figure 3:
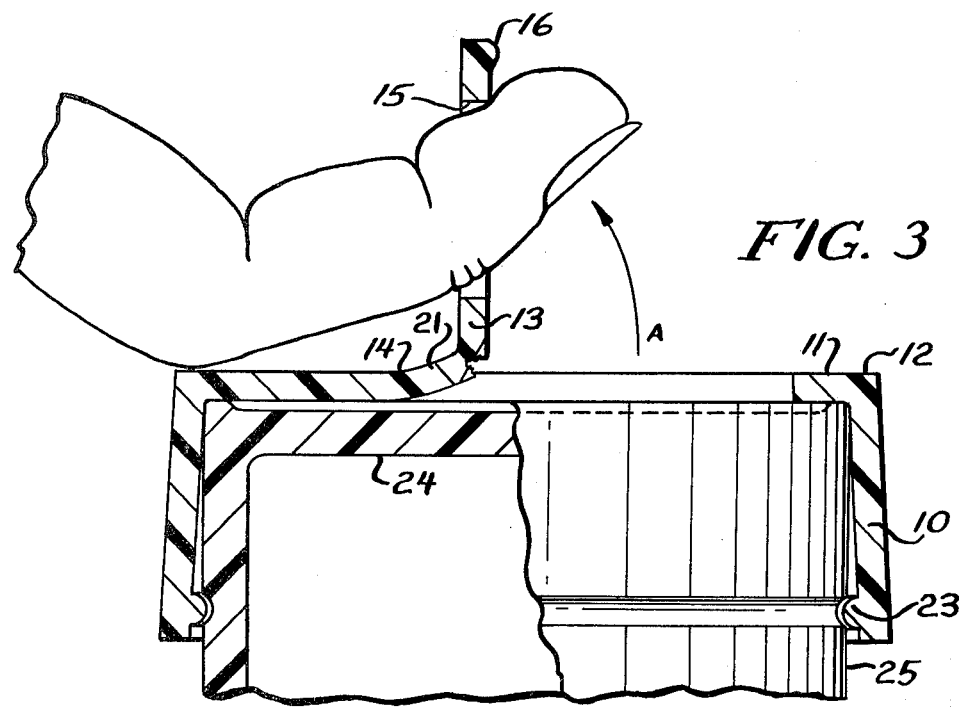
FIG. 3 is an enlarged side elevational view of the hanger assembly in the process of being frangibly activated into operation.

FIG. 2 illustrates an embodiment of the hanger assembly which may be used with discrete rather than integrally molded containers. Such discrete or separate containers (not shown) are glass or plastic and are snapped into the cup-shaped hanger system substantially as shown in FIG. 3 and as will be further discussed below. This embodiment of the hanger system is the preferred embodiment of this invention. It includes the skirt 10, a first flange 11 projecting inward of the upper skirt rim 12, a ridge or second flange 23 for connecting communication with a bottle, a score hinge 18, a resilient lip 21 and a suspending means 17 including a loop 16 and a passage 15. The tab 13 is formed so that it substantially rigidly projects into the opening defined by the flange 11 or the skirt 10 at a downward angle of about 5° to 30°, generally about 20° from the plane of the flange. This ensures that the tab will not inadvertently protrude slightly above the rim 12 due to stresses in the hanger assembly when it is forced onto the base of a bottle if the tab projects outside of the bottom plane of the flange. The bottle will not sit flat on its base. The resilient displacement lip 21 permits the tab to be pressed into the plane of the flange by a bottle base (24 in FIG. 3) without breaking the tab.

FIG. 3 demonstrates a representative technique for frangibly activating the hinge. Bottle 25 is grasped in one hand (not shown) and a finger as shown is worked under the tab through the suspension means passage 15. The finger is contracted or pulled back in the direction indicated by arrow A so as to lift the tab in a direction up and away from the plane defined by the skirt rim 12. Lifting the tab through an arc of about 20° will rupture the restraining elements of the hinge, i.e., the bridges 20 and the hinge 18.

Figure 4:
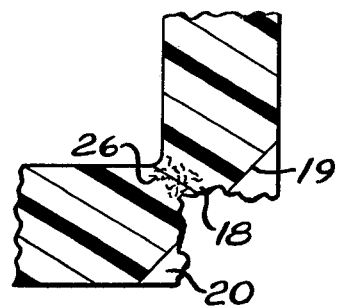
FIG. 4 is an enlarged sectional view of the frangibly-activated hinge after it has been opened.

As shown in FIG. 4, the bridge 20 will be entirely fractured, while the hinge element is stretched and crevassed as generally shown at 26. The resulting frangibly-activated hinge is a fraction of its thickness prior to breakage, generally 50-75% of the unscored thickness. However, the principle contributor to flexibility of the hinge is the multiple fracturing of the hinge material along the length of the hinge; the material contains a great plurality of cracks, none of which is sufficient to separate the hinged components but which create a multiplicity of thin membranes. This thin thermoplastic laminae forms a flexible hinge. In addition, scoring the tab half way through results in a hinge that returns the suspension means to a vertical position if it is forced back more than 90° from its position before hinge activation. This is to be distinguished from scored metal hinges, in which nothing is broken until the metal fatigues and fails.

Suitable materials for making the frangibly-activated hinges used in the hanger assembly of this invention are generically termed hingeable organic polymers. Specific examples include polypropylene or mixtures of polypropylene and polyethylene. Other such polymers will be readily known to the ordinary artisan. A general test is that a 0.05 inch thick layer of polymer which is hinge-scored to a depth of 0.025 inch must be able to survive at least 100 flexings through 100° without separating. The hingeable organic polymer will generally combine to make up the resilient lip and the hinge together. However, that combination can be connected by conventional techniques to the flange and skirt which can be fabricated from any suitable material such as metal or plastics. The hanger assembly may be molded integral with a container. For example, the skirt may be extended or molded with other bottle elements to form the sides and top of a container or bottle. In this case the bottom of the bottle will be in the same position as the bottle bottom 24, but the flange 11 will be integrally molded into the bottle. Other equivalent embodiments will be readily apparent to the artisan.

Other suspension means than the loop of the preferred embodiment will also be apparent. For example, clips or snaps can be provided for connecting the suspension tab to complementary racks or stands.

The containers which are preferred to be used with the hanger assembly herein are parenteral solution administration bottles. Such bottles are especially characterized by the presence of fluid level indicia on the sides of the bottles and sterile closures at the fluid outlet. Such bottles are well known to the ordinary artisan, as are the sterile aqueous solutions of nutrients, drugs and electrolytes contained therein for parenteral administration.

I claim:

1. A method for hanging an article, said article connected to a hanger assembly having a skirt with an upper rim and a tab substantially rigidly appending inwardly from said skirt in a plane substantially parallel to that which is defined by the rim of said skirt, said tab including (a) a suspension means for suspending the article, (b) a frangibly-activated hinge spaced between the skirt and the suspension means, and (c) means interposed between the hinge and skirt for resilient displacement of the suspension means along an axis generally parallel to that of the skirt whereby shock and stress on the hinge is adsorbed, the method comprising applying sufficient force to the suspension means in a direction generally perpendicular to the plane defined by the rim of the skirt to break a portion of the hinge and thereby allow rotation of the suspension means about the hinge.

2. The method of claim 1 wherein the force is applied under the plane of the rim.

3. The method of claim 1 wherein the portion of the hinge that is broken is a layer of hingeable organic polymer.

4. The method of claim 1 wherein the suspension means is rotated about the hinge to a position greater than about 90° from its original orientation in the plane of the skirt rim and said frangibly-activated hinge biases the suspension means back to a position of about 90° from its orientation in the plane of the skirt rim.

5. A hanger assembly comprising a skirt having an upper rim and a tab substantially rigidly appending inwardly from said skirt in a plane substantially parallel to that which is defined by the rim of said skirt, said tab including (a) a suspension means for suspending the article, (b) a frangibly-activated hinge spaced between the skirt and the suspension means and (c) means interposed between the hinge and skirt for resilient displacement of the suspension means along an axis generally parallel to that of the skirt whereby shock and stress on the hinge is adsorbed.

6. The assembly of claim 5 wherein the tab extends inwardly of the circumference of the skirt rim.

7. The assembly of claim 5 wherein the hinge comprises a linear score extending across the tab at about the center axis of the skirt.

8. The assembly of claim 7 wherein the score extends to a depth of about one-half of the way through the tab.

9. The assembly of claim 8 wherein the score is V-shaped.

10. The article of claim 5 wherein tab protrudes from said upper rim down and into the opening defined by said skirt at an angle of about from 5° to 30° from the plane defined by said upper rim.

11. The article of claim 10 wherein the skirt is a cylinder.

12. The article of claim 5 wherein the upper rim of said skirt is a flange projecting into the opening defined by said skirt.

13. The article of claim 5 wherein the means for resilient displacement is a lip of flexible organic polymer.

14. The article of claim 5 wherein the tab comprises a hingeable polymer having a score line intermediate the skirt and the suspension means.

15. The article of claim 5 wherein the suspension means is an opening in the tab.

16. The article of claim 5 wherein the upper rim of said skirt is notched adjacent the point at which said tab extends furthest into the opening defined by said skirt, thereby facilitating access to the end of the tab for bending the tab and breaking the frangibly-activated hinge.

17. A unitary bottle hanger assembly comprising a substantially cylindrical skirt having an upper rim including a flange projecting inwardly of the rim an elongated tab essentially composed of a hingeable organic polymer (a) joined to the flange at a connecting region and (b) substantially rigidly extending at an angle of about from 5° to 30° measured from the plane of the flange into the opening in the skirt defined by the flange, said tab having (a) a passage through the end of the tab opposite the connecting region and (b) a linear score across the tab between the passage and the connecting region, said score located across about the central axis of the skirt and on the side of the tab opposite from the upper rim of the skirt.

18. The hanger of claim 17 wherein the tab occupies about from 20-45% of the circumference of the flange.

19. The hanger of claim 17 wherein the skirt comprises means for connectively engaging a container.

20. A unitary bottle hanger assembly composed of a hingeable organic polymer, said hanger comprising a cylindrical skirt having an upper rim, a first flange projecting inwardly of the upper rim and a second flange projecting from the interior of the skirt below said first flange, an elongated tab joined at a connecting region to the first flange over about 40% of the circumference of the first flange and occupying substantially all of and biased substantially rigidly into the opening in the skirt defined by said first flange, said tab comprising (a) a generally triangular passage through the end of the tab opposite the connecting region, (b) a linear score across the tab between the passage and the connecting region, said score crossing the central axis of the skirt and located on the side of the tab opposite from the upper rim of the skirt, and (c) a means interposed between the hinge and connecting region for resilient displacement of the end of the tab along an axis generally parallel to that of the skirt.

21. The hanger of claim 20 which is free of fasteners for coacting with the tab to bias said tab substantially rigidly into said opening.

22. A combination comprising the hanger assembly of claim 20 and a container.

23. The combination of claim 22 further comprising a sterile solution of nutrient, electrolyte or drug within the container.

24. The combination of claim 23 wherein the container is marked with indicia showing solution level in the container.

25. In a bottle hanger assembly having a skirt with a flange projecting inwardly of the upper rim and a tab joined to the flange, said tab having a suspension means for hanging the assembly and a score for hinging the tab, the improvement comprising means for biasing the tab into the opening in the skirt defined by the flange and means interposed between the score and the flange for resilient displacement of the end of the tab along an axis generally parallel to that of the skirt.

* * * * *